(12) United States Patent
Kulkarni et al.

(10) Patent No.: US 6,342,484 B1
(45) Date of Patent: *Jan. 29, 2002

(54) METHOD AND COMPOSITIONS FOR PROMOTION OF WOUND TREATMENT

(75) Inventors: Anil D. Kulkarni, Manchester, MO (US); Charles T. Van Buren; Frederick B. Rudolph, both of Houston, TX (US)

(73) Assignees: Board of Regents, The University of Texas Systems, Austin; William Marsh Rice University, Houston, both of TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/012,367

(22) Filed: Jan. 23, 1998

Related U.S. Application Data

(63) Continuation-in-part of application No. 08/309,958, filed on Sep. 21, 1994, now Pat. No. 5,712,256, which is a continuation of application No. 08/086,346, filed on Jun. 30, 1993, now abandoned.

(51) Int. Cl.$^7$ ......................... A61K 48/00; A61K 9/127; A61K 31/70
(52) U.S. Cl. ............................. 514/44; 514/43; 514/45; 514/46; 514/47; 424/450
(58) Field of Search ............................. 514/45, 44, 43, 514/47; 424/450

(56) References Cited

U.S. PATENT DOCUMENTS

| | | | |
|---|---|---|---|
| 4,308,257 A | 12/1981 | Caspe | 424/180 |
| 4,486,439 A | 12/1984 | Studt et al. | 424/263 |
| 4,841,962 A | * 6/1989 | Berg et al. | 128/156 |

(List continued on next page.)

FOREIGN PATENT DOCUMENTS

| WO | WO 83/00436 | 2/1983 |
|---|---|---|
| WO | WO 89/10129 | 11/1989 |

OTHER PUBLICATIONS

Aboyants et al., "Treatment of gastric and duodenal ulcer—involves using collagen soln. coupled with methyl–uracil to reduce deformation of mucous during healing process," Abstract dated May 30, 1988.

Belardinelli et al., "The cardiac effects of adenosine," *Progress in Cardiovascular Diseases*, XXXII(1):73–97, 1989.

DeLucchi et al., "Effects of dietary nucleotides on the fatty acid composition of erythrocyte membrane lipids in term infants," *Journal of Pediatric Gastroenterology and Nutrition*, 6:568–574, 1987.

Fanslow et al., "Effect of nucleotide restriction and supplementation on resistance to experimental murine candidiasis," *Journal of Parenteral and Enteral Nutrition*, 12(1):49–52, 1988.

Kulkarni et al., "Influence of dietary nucleotide restriction on bacterial sepsis and phagocytic cell function in mice," *Arch Surg.*, 121:169–172, 1986.

Kulkarni et al., "Modulation of delayed hypersensitivity in mice by dietary nucleotide restriction," *Transplantation*, 44(6):847–849, 1987.

Kulkarni et al., "Immunohemopoietic effects of dietary nucleotide restriction in mice," *Transplantation*, 53(2):467–472, 1992.

Pizzini et al., "Dietary nucleotides reverse malnutrition and starvation–induced immunosuppression," *Arch Surg.*, 125:86–90, 1990.

Rudolph et al., "Role of RNA as a dietary source of pyrimidines and purines in immune function," *Symposium Proceedings, Supplement to Nutrition*, 6(1):45–52, 1990.

Van Buren et al., "Dietary nucleotides, a requirement for helper/inducer t lymphocytes," *Transplantation*, 40(6):694–697, 1985.

Wyatt et al., "Adenosine stimulates glycolytic flux in isolated perfused rat hearts by a1–adenosine receptors," *American Journal of Physiology* 257 (*Heart Circ. Physiol.* 26):H1952–H1957, 1989.

Sigma Chemical Company, "Biochemicals organic compounds for research and diagnostic reagents," published 1992 by Sigma Chemical Co., pp. 42–55, 888–891, 958–961, 1462, 1511, 1521, 1729–1733, 1736, 1737 and 1740.

Wyngaarden et al., "Cecil Textbook of Medicine," published 1988 by W.B. Saunders (Phialdephia, PA), pp. 1980–1984.

Levenson and Demetriou, "Metoblic factors," In: *Wound Healing: Biochemical & Clinical Aspects*, Cohen et al., Eds., W.B. Saunders Company, Philadelphia, pp. 248–273, 1992.

Daly et al., "Enternal nutrition with supplemental arginine, RNA, and omega–3 fatty acids in patients after operation: Immunologic, metabolic, and clinical outcome," *Surgery*, 112(1)56–67, 1992.

Stepan et al. Effect of Local Application of Adenine on the Growth of Granulating Tissue of Rats. Scripta Medica, vol. 58, pp. 495–502, 1985.*

*Primary Examiner*—Deborah J. Clark
(74) *Attorney, Agent, or Firm*—Fulbright & Jaworski, LLP

(57) ABSTRACT

The present invention comprises compositions and preparations for the promotion of wound healing in an animal. Methods for preparing the compositions as well as methods for using the compositions to achieve the promotion of wound healing, are also provided. The composition may comprise a dietary regimen or a therapeutic agent. These compositions include a wound healing promoting concentration of nucleotides. By way of example, such nucleotides may comprise RNA, adenine, uracil or a mixture thereof. The compositions can be prepared as suitable for oral, parenteral, intravenous or topical administration. Methods for using the preparation as a treatment to enhance the healing of an already existing wound or for use as a pretreatment regimen for animals in anticipation of surgery, are also disclosed.

31 Claims, 4 Drawing Sheets

U.S. PATENT DOCUMENTS

| | | | |
|---|---|---|---|
| 4,912,092 A | 3/1990 | Gruber | 514/45 |
| 4,994,442 A | 2/1991 | Gil et al. | 514/45 |
| 5,066,500 A | 11/1991 | Gil et al. | 426/72 |
| 5,246,708 A | 9/1993 | von Borstel et al. | 424/450 |
| 5,712,256 A | 1/1998 | Kullarni et al. | 514/44 |

* cited by examiner

METHOD AND COMPOSITIONS FOR PROMOTION OF WOUND TREATMENT

This is a continuation-in-part of U.S. Ser. No. 08/309,958, filed Sep. 21, 1994 now U.S. Pat. No. 5,712,256, Jan. 27, 1998, that is a continuation of U.S. Ser. No. 08/086,346, filed Jun. 30, 1993, abandoned.

The United States government has a paid-up license in this invention and the right in limited circumstances to require the patent owner to license others on reasonable terms as provided by the terms of Grant No. RO1-CA3 5492 awarded by National Institutes of Health.

BACKGROUND OF THE INVENTION

1. Field of the Invention

This invention relates generally to techniques used in the promotion of wound healing. In particular, compositions of matter that promote the healing of wounds, methods of manufacture of wound healing promoting compositions, and methods of treatment that promote wound healing are encompassed within the scope of the present invention.

2. Description of the Related Art

Animals, including human beings are susceptible to a barrage of normal cuts and scrapes, as well as to much more serious wounds that may require medical attention.

Wounds may be the result of accidents or surgery. For the most part, such wounds heal at a fairly steady and slow rate, being affected by many factors including the nature and site of the wound and the physiological state of the animal.

The process of wound healing involves many complicated components. Immediately upon the injury insult, defense mechanisms inherent in normal body tissues are activated to restore continuity and tensile strength. Wound healing then occurs in three distinct phases.

First, is the phase of acute inflammatory response. Body fluids containing plasma proteins, fibrin, antibodies and various blood cells flow into the wound. Scab formation takes place and inflammation occurs within a few hours. Also, at this stage, neutrophils, monocytemacrophages come into play. During this acute phase, the wound is solely dependent on the closure material contained in the scab for strength.

Second, is the phase of fibroplasia. Here, via various enzymatic mechanisms, fibrin synthesis and accumulation takes place. This causes an increase in wound tensile strength and stimulation of fibroblast proliferation and growth. Fibroblasts secrete collagen, a fibrous protein as part of connective tissue. Collagen deposition begins from the fifth day and results in rapid gain in tensile strength of the wound.

The third phase is the maturational process. Tensile strength continues to increase from the cross-linking of collagen fibers. Deposition of fibrous connective tissue causes scar formation.

Collagen production is vital for the wound healing process. Collagen is the most prevalent protein in animals. It is an obligatory constituent of connective tissues and extra cellular matrices. Collagen networks in the tissues are responsible for establishing and maintaining the physical integrity of diverse extra cellular structures. Collagen, at molecular level, is defined as a protein comprised of lengthy domains of triple-helical confirmation. Collagenous scaffolding of extra cellular matrix includes genetically distinct types of collagen. During the normal wound repair, collagen neosynthesis and deposition of type III collagen is demonstrated in the earliest phase, i.e. 24 hr to 48 hr, period. From that point, a significant increase in type I collagen is associated with the mature wound fibroblasts and subsequent healing events. Because of its important role in the wound healing process, collagen production is a measure of the rate and quality of wound healing. As such, assays that measure collagen production are useful in experimental models to study wound healing.

The healing process is very much organ and tissue-type dependent. For example, intestinal tissue is physiologically a rapidly self emphasizing tissue and unlike other organs in that it must constantly be repaired. Intestinal repair is an ongoing process necessary to maintain normal function of the intestines. There is an almost constant need for repair in the intestines, where injury arises from aberrations in the digestive process or from ingested foods. In contrast to intestinal repair, the "wound healing" discussed in this application is caused by external factors of trauma and injury. Such sudden and external trauma injury requires intact and able host defense mechanisms.

The process of wound healing involves a complex system of local and remote (systemic) energy and substrate requirements and uses. For example, amino acids and sugars are needed as substrates for collagen and proteoglycan synthesis. Migration of fibroblasts and epithelial/endothelial cells during the wound healing process places additional systemic demands on the animal during the wound healing process. Wounded tissues have unique nutritional needs and physiological features. Lymphocyte participation in wound healing has been demonstrated (Peterson et al. (1987)). Alteration in the hosts T-cell dependent immune response has also been shown to influence wound healing. Cyclosporine and anti T-cell antibodies, both of which interfere with T-cell function, abrogate wound healing. Similarly, macrophages and their products are also involved in wound healing. Increased circulation usually results in rapid delivery of monocytes and PMN's to the wound site. This in turn results in the elimination of bacterial contamination of the wound due to nonspecific killing mechanisms and also enhances the rate of wound healing. These various cell types are synthesized by the bone marrow.

In many cases, the wound healing process proceeds very slowly, particularly in animals having limited energy stores or diets low in energy substrate sources.

Purine and pyrimidine nucleotides are involved in almost all cellular processes and play a major role in structural, metabolic, energetic and regulatory functions. They make up the monomeric units of RNA and DNA; RNA synthesis is required for protein synthesis and DNA synthesis is required for growth and cell division. Adenosine triphosphate, an adenine nucleotide is the major source of chemical energy used in metabolism, driving almost all cellular processes. Nucleotides are physiological mediators in a number of metabolic processes. Cyclic adenosine monophosphate (cAMP) and cyclic guanosine monophosphate (cGMP) regulate a large number of cellular events, and adenosine is important in regulating blood blow and smooth-muscle activity. Guanosine triphosphate (GTP) is involved in signal transduction, RNA structure, and microtubule formation. Many other nucleotides are involved in regulating other cellular processes. Nucleotides function as activated intermediates in the synthesis of glycogen and glycoproteins; they are also intermediates in the synthesis of phospholipids, and serve as methyl and sulfate donors. They are structural components in a number of coenzyme that are crucial in many metabolic pathways, and they function as allosteric effectors that control the regulatory steps of major metabolic pathways.

Nucleotides consist of a nitrogenous base (either a purine or a pyrimidine), a sugar, and one or more phosphate groups. The term nucleotide in the context of the title refers to the multiple forms in which purines and pyrimidines are found and does not imply a specific form of the compounds but all forms that contain purine and pyrimidine bases.

The major purine bases are adenine, guanine, hypoxanthine and xanthine. Uric acid is also found in significant levels. The major pyrimidine bases are uracil, thymine, and cytosine. Other pyrimidines and purines are also present in smaller amounts and they have significant roles particularly in RNA structure and function.

However, the nucleotides that occur in the free form in cells are predominantly those having the phosphate group in the 5' position, since the enzymatic reactions normally involved in nucleic acid synthesis and breakdown in cells proceed via nucleoside 5'-phosphates intermediates. Table 1 gives the nomenclature of the major ribonucleoside 5'-monophosphates (also called 5'-ribonucleotides) and deoxyribonucleoside 5'-monophosphates (also called 5'-deoxyribonucleotides). All the common ribonucleosides and 2'-deoxyribonucleosides also occur in cells as the 5'-diphosphates and the 5'-triphosphates, i.e., the 5'-pyrophosphoric and the 5'-triphosphoric acid esters of the nucleosides.

TABLE 1

Nomenclature of bases, nucleosides, and nucleotides

| Base | Ribonucleoside | Ribonucleoside 5'-mono-, di-, and triphosphates Abbreviations | | | Deoxyribonucleoside | Deoxyribonucleoside 5'-mono, di-, and triphosphates | | |
|---|---|---|---|---|---|---|---|---|
| Adenine (A) | Adenosine | AMP | ADP | ATP | Deoxyadenosine | dAMP | dADP | dATP |
| Guanine (G) | Guanosine | GMP | GDP | GTP | Deoxyguanosine | dGMP | dGDP | dGTP |
| Uracil (U) | Uridine | UMP | UDP | UTP | | | | |
| Cytosine (C) | Cytidine | GMP | CDP | CTP | Deoxycytidine | dCMP | dCDP | dCTP |
| Thymine (T) | | | | | Deoxythymidine | dTMP | dTDP | dTTP |

The nucleotides are phosphoric acid esters of nucleosides in which the phosphoric acid is esterified to one of the free pentose hydroxyl groups. Nucleotides occur in free form in significant amounts in a variety of cell types. They are also formed on partial hydrolysis of nucleic acids, particularly by the action of a class of enzymes called nucleases. Nucleotides containing 2-deoxy-D-ribose are deoxyribonucleotides; those containing D-ribose are ribonucleotides. A nucleoside, which does not have a phosphate group, is formed from a base and a pentose via a glycosidic bond between the N-1 nitrogen of a pyrimidine or the N-8 of a purine and the C-1' carbon of the pentose. The pentose is ribose or 2'-deoxyribose. The major function of the 2'-deoxyribose nucleotides is in DNA. The ribonucleotides are the monomeric units of RNA but also serve in most other cellular and metabolic functions of nucleotides. The phosphoryl group of nucleotides is most commonly esterified to the C-1' hydroxyl of the pentose. In cyclic nucleotides the phosphate is esterified to both the C-5' and C-3 hydroxyl groups. The number of phosphate groups attached is indicated by a mono-, di- or tri-designation. In the discussion and description of the claims the term nucleotide will be used generally to mean a source of preformed purines and/or pyrimidines in various forms including RNA as well as individual purines and/or pyrimidines as bases, nucleosides or nucleotides. It does not generally (except as noted in specific examples) imply that one form is required.

Since there are two or more free hydroxyl groups in nucleosides, the phosphate group of nucleotides can potentially occur in more than one position on the sugar ring. In the case of deoxyribonucleotides, there are only two possible positions in 2-deoxyribose that can be esterified with phosphoric acid, namely, the 3' and 5' positions. Both 3'- and 5'-deoxyribonucleotides occur biologically. In the case of ribonucleotides, the phosphate group may be at the 2', 3', or 5' position; all 3 types of ribonucleotides have been found as hydrolysis products of RNA, depending on conditions. Cyclic monophosphates of adenosine are also possible.

Purines and pyrimidines can be formed by de novo biosynthesis or salvage of preformed bases and interconversion to the desired compound. Almost all of the atoms in both bases are derived directly or indirectly from amino acids. Phosphoribosylpyrophosphate (PRPP) serves as the pentose source for both purine and pyrimidine biosynthesis and for salvage of bases. PRPP is formed from ribose-5-phosphate. Deoxyribonucleotides are subsequently formed from the ribonucleotides.

The pathway for purine biosynthesis consists of ten steps. The initial step involving PRPP and glutamine condensation catalyzed by PRPP aminotransferase is likely the rate limiting step and is feed-back inhibited by AMP and GMP. IMP is the first purine formed and it is converted to either AMP or GMP depending on cell needs. Regulation occurs at these steps also. The monophosphates of both purines and pyrimidines are readily converted to di- and triphosphates by various kinase enzymes using ATP as a phosphate source.

In pyrimidine biosynthesis, PRPP is not added until the intact pyrimidine is formed as orotic acid. OMP (orotidine-5'-monophosphate) is the first pyrimidine formed but it functions in the cell only as a precursor of other pyrimidines. UMP is formed from OMP and then CTP and TTP are derived from UMP. In eukaryotes regulation of pyrimidine synthesis occurs primarily at carbamoyl phosphate synthesis with inhibition by pyrimidine nucleotides and activation by purine nucleotides.

Deoxyribonucleotide synthesis is catalyzed by ribonucleotide reductase, an enzyme that converts both purine and pyrimidines to their deoxyribose forms. The reductase is controlled in a complex manner by both substrates and product to allow synthesis of equimolar levels of the various deoxyribonucleotides. Since the deoxynucleotides are used only for DNA synthesis the levels of the purine and pyrimidine need to be equal. Thymidine triphosphate is then formed as the monophosphate from deoxy-UMP. The levels of the deoxyribonucleotides are typically in the range of 2–60 mM while ribonucleotides are typically much higher with ATP concentration in the range of 2–10 mM and other ribonucleotides from 0.05–2 mM. Di- and monophosphates are typically lower than the triphosphates. Levels of both ribo- and deoxyribonucleotides will vary considerably depending on the phase of the cell cycle and under various metabolic conditions.

In primates uric acid is the end product of purine catabolism while other species can convert it to more soluble forms. The end products of pyrimidine catabolism are β-alanine and β-amino isobutyrate which are both soluble and easily excreted. Less is known about pyrimidine catabolism since no clinical effects of the end products occur. The catabolic pathways operate in the digestive system converting DNA and RNA and free nucleotides to nucleosides and free bases. Pyrimidine bases and nucleosides are taken up and readily incorporated into tissues. Dietary nucleotides appear to be important in support of cellular metabolism particularly in rapidly dividing tissues such as lymphoid cells and the intestine.

The uptake of purines and pyrimidines from the intestine and cellular turnover of nucleotides particularly from mRNA provides preformed bases that avoid the metabolic cost of de novo biosynthesis. Synthesis of both purines and pyrimidine consumes a significant amount of energy. It is important to note that role of amino acids in nucleotide synthesis and the salvage of dietary and cellular sources of nucleotides. A balance exists between these different pathways affording proper levels of nucleotides in cells with minimal metabolic expense.

The usefulness of dietary nucleotides in certain medical contexts is documented. The instant inventors and others have described the potential role of dietary nucleotides in several contexts. For example, dietary nucleotides are required for maintenance and recovery of host immune response (Van Buren et al. (1983) and Rudolph et al. (1990)). It has also been shown that there is increased activity of Lyt1+, IL2-R+ and Mac1+ cells in the tissues responding to alloimmune challenge (Van Buren et al. (1985) and Kulkarni et al. (1988)). Nucleotide supplementation has also been shown to provide an increase in both immunohemopoiesis (Kulkarni et al. (1992)) and resistance to infectious microorganisms (Kulkarni et al. (1986)). Nucleotide supplementation has also been described as reversing immunosuppression induced by protein starvation. (Pizzini et al. (1990)).

Several research groups have published works concerning the relationship of nucleotides to immune system functioning. Van Buren et al. (1985) relates to the role of dietary nucleotides in the processes of recognition of and sensitivity to foreign antigens and in lymphocyte proliferation to alloantigen or lectin stimulation. The present inventors have also described the importance of dietary sources of pyrimidines and purines, such as those in nucleic acids, in immune function and on gastrointestinal function. (Rudolph et al. (1990)) Normal cellular immune response has therefore been postulated to require a source of preformed nucleotides. The authors conclude that dietary sources of nucleotides are important to support optimal growth and function of metabolically active cells such as lymphocytes, macrophages and intestinal cells.

The role of dietary nucleotides in the immune response is further examined in Pizzini et al. (1990). In this series of studies, nucleotide restriction was tested using both a starvation malnutrition and a protein malnutrition in vivo model. Animals in the starvation malnutrition study receiving a diet supplemented with yeast RNA prior to the period of starvation (5 days) reportedly demonstrated an increase in spontaneous concanavalin A and phytohemagglutinin-stimulated blastogenesis in in vitro assays. In protein malnutrition studies, the return to any of the examined diets (chow diet, nucleotide-free diet, or nucleotide free diet supplemented with 0.25% yeast RNA) reportedly resulted in restoration of body weight, while only the RNA-supplemented and chow diets restored popliteal lymph node immune reactivity.

The usefulness of nucleotides in the repair or regeneration of intestinal gut cells in infants was the basis of the U.S. Pat. No. 4,994,442. This patent relates to a milk and non-milk based infant formula that includes nucleosides and/or nucleotides. As previously stated, this process of intestinal repair is continual and physiologically distinct from wound healing in response to trauma or insult, which is the goal of the present invention.

The role of dietary nucleotides in preventing the onset of infection has also been studied. In Kulkarni et al. (1986), the present inventors present data relating to the role of dietary nucleotides (for example, dietary adenine, uracil or RNA) in maintaining animal resistance to *Staphylococcus aureus*. Fanslow et al. (1988) examines the relationship between dietary nucleotides and animal susceptibility to candidiasis. Studt et al. (U.S. Pat. No. 4,486,439) relates to a method for treating coccidial infections employing a formulation that includes, among other ingredients, 2-pyrimidine, 4-pyrimidine, 5-pyrimidine, 6-pyrimidine, 2-purine, 6-purine, 8-purine or 9-purine.

Dietary nucleotides have been implicated as having a role in relation to delayed cutaneous hypersensitivity (Kulkarni et al. 1987) and in the fatty acid composition of erythrocyte membrane lipids in infants (DeLucchi et al. 1987).

Gil et al. (U.S. Pat. No. 5,066,500) relates primarily to a non-milk based infant formula that includes amino acids and is enriched with nucleotides and/or nucleosides (at least one of uridine, uridine-phosphate, guanosine or guanosine phosphate, adenosine or adenosine phosphate, cytidine or cytidine phosphate, inosine or inosine phosphate, or mixtures thereof). Examples are also provided of defined composition dietary supplements for adults suffering from such non-trauma or insult problems as energy-protein malnutrition, hypercatabolism, malabsorption-malnutrition syndromes, severe homeopathy, or chronic hematopathy. However, these formulations are not used to stimulate the immune system. Gut intestinal cell turnover is a normal, physiologic process, in which the inflammatory response plays no role. Healing of a traumatic wound, on the other hand, requires an inflammatory response as a necessary first step in wound healing.

A respiratory enzyme booster tablet that includes a combination of diphosphopyridine nucleotide, nicotinamide, adenosine-5-monophosphate and a carrier has been described in the Case patent (U.S. Pat. No. 4,308,257). The compound functions as a co-enzyme that acts in the cellular respiration process. An injectable treatment that includes diphosphopyridine nucleotide is also described. The use of a nucleotide compound in the absence of other ingredients however, has not been described, nor suggested as a potentially useful therapeutic agent. Also, these tablets are specifically designed to increase the rate of cellular respiration, a phenomenon that occurs in all cells. These formulations do not appear to play a role in the enhancement of collagen formation or wound-healing.

The Guari patent (EP No. 85,084, 1983) relates to a wound-healing and antiviral preparation which includes a dialysis concentrate of deproteinated calf s blood and a member of a very specific class of furanosylated, uracil derived compounds. These ingredients reportedly act "synergistically" to provide the described physiological effects.

The idea and process of nutritional therapeutic approach would have no side effects (toxic or untoward) as shown many times by the pharmacologic or chemotherapeutic interventions. Injury or trauma induced stress causes sudden loss of body fluids and nutrients, proper nutritional repletion can improve these losses. The effects may be sustaining and long term rather than symptomatic quick-fix afforded by other means. Nutritional modulation may help and improve the endogenous physiologic process in order to combat the wound-related trauma.

In reviewing the known related art, it becomes apparent that there has been no suggestion of the usefulness of nucleotides as pharmacologically active agents in the relatively complex, processes of wound healing. For example, the specific events important in wound healing of collagen formation, fibroblast proliferation and restoration and maintenance of host immune response have not been described or suggested to be enhanced through dietary supplementation with nucleotides.

Normal wound healing can be impaired by chronic infection, protein malnutrition, poor blood supply, vitamin deficiencies, previous radiation exposure, diabetes mellitus, corticosteroid therapy and deficiencies in the components of the host wound response. Obviously, many of these conditions are more likely to cause problems the longer a wound takes to heal. Additionally, escalating health care costs indicate a need for methods that promote wound healing. Therefore, any procedures that would aid in wound healing would be welcomed in the medical field.

SUMMARY OF THE INVENTION

The problems associated with wound healing are in part remedied by the compositions and methods of the present invention. The inventors have found that wound healing can be greatly enhanced by the inclusion of nucleotides and/or substances that include essential nucleotides, such as RNA, DNA, oligonucleotides, purine and pyrimidine bases, or any other source in a pharmaceutical preparation. Dietary nucleotides are also proposed by the present inventors to be useful in pretreatment regimens to enhance wound healing in, for example, surgery patients. The invention provides for the use of nucleotides in concentrations effective to promote wound healing. Great utility is realized with the described compositions and methods in enhancing the rate of wound healing, and the wound healing process in general. A more rapid wound healing process also is anticipated to reduce recovery time. Concomitant benefits would also include a reduction in medical costs and treatment, time away from work, and the incidence and severity of infection.

The inventors have shown that dietary nucleotides modulate various host immune parameters, especially in protein-malnutrition induced stress, nucleotide supplemented diets improve rapidly the host immune system. This has been shown by various in vivo assays examining the immunologic capacity as well, as evidenced by an increased resistance to sepsis observed by the present inventors. It is felt that utilization of exogenously supplied nucleotides by T-lymphocytes and macrophages of the body's immune system is independent of provision of dietary protein. A unique quality of dietary nucleotides heretofore undescribed for any other nutritional substrate improves systemic host immune response, both specific and nonspecific, is therefore provided by the present invention. Such a boost of the immune response then, in turn, responds to the body's requirements for alleviating insults. Such insults would include trauma, injury, either external or internal that would require immediate repair in order to maintain proper body physiology and function. The wound models described in this application examine such cases of injury.

The present invention contemplates a therapeutic agent for the promotion of wound healing. In one preferred embodiment, the therapeutic agent comprises a therapeutically effective concentration of nucleotides (i.e., effective to promote wound healing) in a pharmacologically acceptable carrier. The nucleotides contained in the "active compound" of the therapeutic agent may comprise RNA, adenine, uridine, any of the compounds contained in Table 1, or a combination thereof. In some preferred embodiments of this invention, the nucleotide component comprises RNA, adenine, uridine, inosine or a mixture thereof. While almost any level of nucleotide administration is expected to be of benefit in the wound healing process, it is anticipated that concentrations of about 0.10% to 0.50% (ranging from 0.00034 g/kg body wt/day to 0.17 g/kg body wt/day) will be particularly useful. These concentrations are for purines and pyrimidines in the form of nucleotides in the pure chemical sense, i.e. with a phosphate group. If nucleosides are administered, the concentrations will range from 0.00022 g/kg/day–0.12 g/kg/day, since nucleotides do not contain the weight of a phosphate group. As mentioned previously, the use of the term "nucleotide" elsewhere in the application means both nucleotide and nucleoside forms of the purines and pyrimidines. In the claims, a claim to concentrations of nucleotides, (i.e. 0.00034–0.17 g/kg/day) encompasses the equivalent amount of nucleoside (i.e. 0.00022–0.12 g/kg/day). A concentration of about 0.25% represents a most preferred embodiment of the present invention.

A decided practical advantage is that the nucleotides that comprise the active compounds of the present invention may be administered as a dietary supplement in any convenient manner, such as by the oral, intravenous, intramuscular, or subcutaneous routes. The dosage regimen of this dietary therapy may be adjusted to provide the optimum therapeutic response. For example, several divided doses may be administered daily or the dose may be proportionally reduced as indicated by the exigencies of the therapeutic situation.

The nucleotides may be orally administered, for example, with an inert diluent or with an assimilable edible carrier, or they may be enclosed in hard or soft shell gelatin capsule, or they may be compressed into tablets, or they may be incorporated directly with the food of the diet. Since there is no disagreeable taste to nucleotides, they could be supplied in a powdered form to be mixed with food by the patient. For oral therapeutic administration, the active compounds may be incorporated with excipients and used in the form of ingestible tablets, buccal tablets, troches, capsules, elixirs, suspensions, syrups, wafers, and the like. Such compositions and preparations should contain sufficient active compound so as to administer at least 0.00034 g/kg body weight active compound per day. The percentage of the compositions and preparations may, of course, be varied according to the specifics of a therapeutic situation. The amount of active compounds in such therapeutically useful compositions should be such that a suitable dosage will be obtained when a compositions is administered in a suitable way.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The nucleotides may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Finally, the nucleotides could be supplied topically with a gel, powder, salve, or patch.

As used herein, "pharmacologically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated.

Of course, the nucleotide active compounds of the present invention may be administered by any of the other numerous techniques known to those of skill in the art. (For a reference on these techniques see *Remington's Pharmaceutical Science* $18^{th}$ Edition, (1990)) which is specifically incorporated herein in pertinent part for this purpose). Supplementary active ingredients can also be incorporated into the compositions.

The present invention also is proposed to provide a dietary supplement for the promotion of wound healing. This regimen may comprise a concentration of nucleotides therapeutically effective to promote wound healing in a pharmacologically acceptable carrier solution. The dietary supplement prepared in any suitable form, for example as a liquid suitable for injection, parenteral administration, or oral administration or as powder suitable for mixing with food or a beverage, e.g., as tablets or capsules. It is contemplated that the dietary regimen of the invention may be administered to an animal either as a pretreatment in anticipation of surgery or after a wound has occurred to both hasten and enhance the quality of wound healing.

The present invention also includes methods for promoting wound healing in animals. These methods comprise preparing a composition of nucleotides effective to promote wound healing and treating an animal with an effective concentration of the composition. These methods can be of use in treating a wound that presently exists or a wound that may exist in the future, for example, in the case of a scheduled surgery. Thus, the present formulations may be used as part of a pretreatment plan that would provide a heightened level of nucleotides in the animal prior to surgery that will in turn enhance both the healing process and the rate at which the wound is healed.

It is projected that it will be beneficial to place many, if not all, surgery patients on a nucleotide pre-treatment regimen to promote the more rapid healing of incisions, etc., that occur during surgery. For example, a patient would be given a nucleotide concentration effective to promote wound healing in any of the previously suggested forms from the time of the diagnosis of the need of surgery until a prescribed time post-surgery when the wound has healed satisfactorily. It is projected that nucleotide treatment can be done for an appropriate period prior to surgery. This period may be quite short in a stressed person, but could be as long as a number of weeks.

The present invention also contemplates methods of enhancing the rate of wound healing with the administration of a therapeutically effective concentration of nucleotides to a wounded animal. Such an enhancement will most times also involve an increase in the collagen content of a wounded area.

The present invention contemplates methods encompassing a pretreatment regimen for enhancing the rate of wound healing in an animal that is to undergo surgery. These methods comprise the administration of a therapeutically effective concentration of nucleotides in a pharmacologically acceptable carrier to an animal. A most preferred embodiment the pretreatment method is expected to involve pretreatment for up to around 4 weeks prior to surgery. However, benefits of this method can be expected with shorter lengths of pretreatment. It is anticipated that the preferred embodiments of these pretreatment methods will comprise as active compounds RNA, adenine, uracil or a mixture thereof as the source of nucleotides. Of course, those of skill in the art will understand that other sources of nucleotides will be useful as active compounds in this invention.

The present invention also contemplates a method of preparing a therapeutic agent for the promotion of wound healing comprising placing a wound healing promoting concentration of nucleotides in a pharmacologically acceptable carrier solution. The carrier should provide an adequate means for delivering the nucleotides to an animal in need thereof. This preparation could be in solid form (such as in powdered capsule or tablet form) or in a liquid form (suitable for injection, parenteral or oral administration).

The present invention therefore provides improved therapeutic agents for wound healing, methods for the preparation of these therapeutic agents, and methods for the promotion and enhancement of the rate of wound healing. These compositions and methods are anticipated to provide for a more rapid and complete wound healing in animals. As wound healing is the most catastrophic and costly problem associated with surgery, the advantages of reduced medical complications associated with the healing process and improved quality of wound healing will provide a significant advancement in patient post-surgical clinical management. These and other advantages of the present invention will be further appreciated from the detailed description provided below.

One embodiment of the present invention involves a method for promoting wound healing in a diabetic subject. This involves preparing a dietary composition supplemented with RNA, adenine, uracil, inosine or adenosine in an amount effective for promoting wound healing and feeding the diabetic subject the composition. Another important component of the present invention is a method for promoting wound healing in an animal subject to protein-deficient nutrition. This involves preparing a dietary composition supplemented with RNA, adenine, uracil, inosine or adenosine in an amount effective for promoting wound healing and feeding the protein-deficient animal with the composition. This method is further enhanced if the protein or amino acid source is also fed to the animal at this time.

In one important aspect, the present invention may involve preparing a sterile composition comprising, RNA, adenine, uracil, inosine or adenosine in an amount effective to promote wound healing and topically treating the wound of an animal with the composition. Another important embodiment of the present invention for the promotion of wound healing comprises obtaining a crosslinked collagen mesh. This embodiment further involves obtaining a composition supplemented with RNA, adenine, uracil, inosine or adenosine in an amount effective for promoting wound healing then emplacing the crosslinked collagen mesh on the wound and treating the animal with the composition. The treatment may be topical or enteral, in any manner such that the wound area has increased nucleotide concentrations. The compositions of the present invention may be designed to be intravascularly administered. For example, when a patient is on a parenteral feed, it might be expected that the feed was deficient in amino acids. Thus a parenteral feed comprising the nucleotide compositions described above as well as additional amino acids or proteins may be substituted. Topical administration of the nucleotides and possibly protein or amino acids should also be effective.

DETAILED DESCRIPTION OF THE PREFERRED EMBODIMENTS

Figure 1:
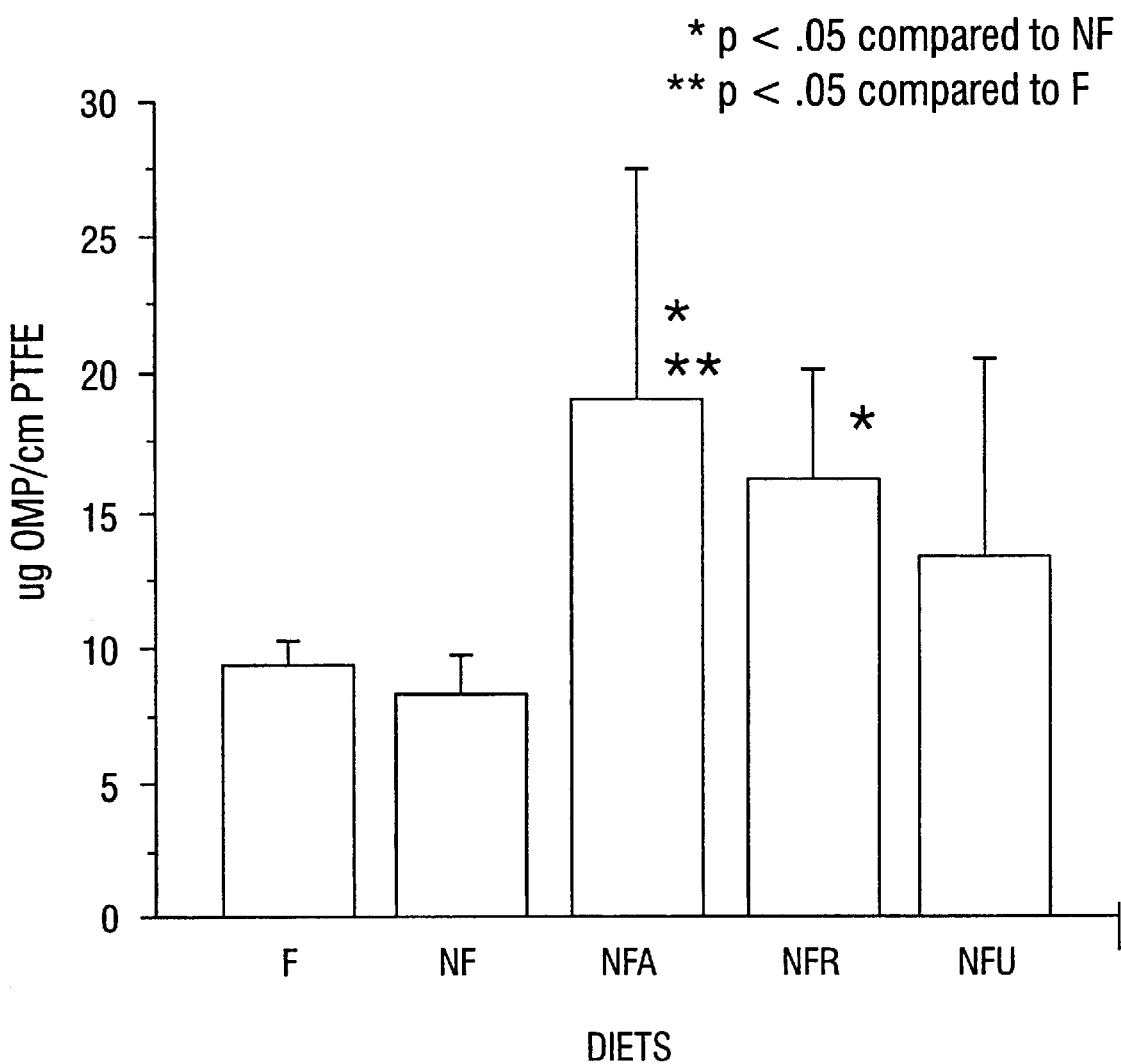
FIG. 1: Wound collagen content of a wound as a function of hydroxyproline (OHP) in mice fed one of the following diets: normal (F), nucleotide free (NF), nucleotide free supplemented with adenine (NFA), nucleotide free with RNA (NFR), nucleotide free with uracil (NFU).

The present invention provides preparations and methods of using the preparations for the enhancement of the quality and rate of wound healing. Methods for preparing the various formulations are also provided. The preparations/formulas of the present invention may comprise a dietary regimen or a therapeutic agent. As a therapeutic agent, the invention comprises a wound healing promoting concentration of nucleotides together in a pharmaceutical acceptable carrier. The therapeutic agents of the invention may be delivered to an organism through any of a number of routes with equal therapeutic efficiency. The methods of the present invention may vary in the means of delivery chosen, the type of organism treated, and the time-frame of the treatment relative to the time of the wounding. There are also a variety of methods of preparing the preparations/formulations encompassed within the contemplated scope of the present invention.

The following examples are intended to illustrate the practice of the present invention and are not intended to be limiting. Although the invention is demonstrated with an RNA nucleotide, other nucleotides having would healing promoting activity may be used in a similar fashion.

MATERIALS AND METHODS

Animals and Diets

Balb/c mice (Jax Labs), 8 weeks old, are typically used in these studies. Custom made diets from a can be obtained from a commercial facility such as Purina Test Diets or produced in the lab.

Animals are maintained on specific diets designed to test the effects of nucleotides on wound healing. An example of one such experimental diet regime, which could be fed diets prior to implantation of wound cylinders could be: Formula chow (F), Basal diet (nucleotide free) (NF), NF supplemented with 0.25% yeast RNA (NFR), or 0.06% uracil (NFU).

A protein starvation model can also be used in conjunction with these studies. In such a protocol, animals are implanted with wound cylinders and on the same day mice are placed on one of the following diets: Protein free (PF), PF supplemented with 0.25% yeast RNA (PFR), and PF supplemented with protein (NF). Mice are maintained on these diets until the day of sacrifice i.e. day 14 from implantation.

Measurement of Collagen Synthesis in Wound Healing

Studies to test the hypothesis that dietary nucleotides are required for collagen synthesis in wound healing can be assessed using the method of Goodson and Hunt 1982). In this protocol, a 2 cm long polytetrafluoroethylene (PTFE) (3 mm lumen, 90 m pore size) would cylinder (WL Gore Associates) is placed subcutaneously in the orsal midline of each animal while each animal is under general anesthesia pentobarbital). Cylinders are then injected with 0.2 ml of phosphate buffered saline. On day 14 or another suitable time, animals are sacrificed and intact wound cylinders retrieved and frozen until analysis for hydroxyproline content and collagenase assay.

The hydroxyproline assay is performed as follows. A portion of wound cylinder implant from each animal is used for preparing acid hydrolysates for measuring hydroxyproline concentrations in this assay using the method of Woessner (1961), which reference is specifically incorporated herein by reference for this purpose. The hydroxyproline concentration within each implant, a measure of collagen content can be determined spectrophotometrically and expressed as micrograms of hydroxyproline per centimeter of PTFE implant.

Collagenase plays a significant role in wound healing. In the wound repair process, collagen synthesis and accumulation is important. Careful and appropriate degradation of collagen is very important in wound healing repair and tissue formation. The collagen fibril, formed as required by aggregation of collagen monomers, is extremely effective structural element for maintaining the integrity of the newly formed connective tissue. These fibrils are physically stable up to 50° C. and are chemically resistant. Fibrillar collagen is essentially insoluble under normal physiological conditions. It is resistant to degradation action of a wide range of naturally occurring proteolytic enzymes. However, host cells have the ability for endogenous production of specific enzymes—collagenases—which act primarily on collagen. These enzymes, by proteolytic cleavage denature each of collagen fibers. Thus for appropriate wound healing and formation of repair-tissue and its structural integrity, endogenous production of collagenase is essential. The measurement of collagenase in wound tissue is an indicator of wound healing strength. For this assay, one can use a collagenase assay system such as the one available from New England Nuclear (NEN-cat# NEK016), employing 3H-collagen. Collagenolytic activity is monitored with a high specific activity substrate by quantitating the production of soluble radioactive fragments, which are readily separated from undigested collagen fibrils by centrifugation.

The hydroxyproline assay and the collagenase assays, as discussed above, lend themselves to both the nucleotide supplemented and the protein starved animal models.

Colonic Tensile Strength and Wound Healing with Nucleotides

Studies can be conducted to determine whether dietary nucleotides improve colonic wound bursting (tensile) strength. The colonic tensile strength model relates to the type of tissue that is highly dependent on rapid fibroblastic regeneration and formation of a strong matrix. This means rapid accumulation of collagen fibers in the wound. The reparative collagen and its fibers deposition attributes to the strength of the tissue which is measured by the model described by Nelsen and Anders (1966), referred in the reference section and specifically incorporated herein in pertinent part.

This method involves testing the bursting strength of intestinal anastomoses by distention with either air or water. The traction method of testing bursting strength can also be employed. Lengths of ileal small bowel, usually around 6-8 cm, are isolated and divided in the middle with proper surgical techniques and resutured as end to end anastomosis (using appropriate sutures). These surgical procedures and techniques should be identical in all the animals involved in a particular study, and is a general surgical technique well known to those of skill in the art. On post-operative day 14, or at another suitable time, the animals are sacrificed and the operative area of ileal gut, with the anastomosis in the center, removed for the bursting strength evaluation. All the segments are typically adjusted to an identical collapsed length, attached at both ends to grooved rubber stoppers and securely tied with cotton tapes. Air is removed and the segment is then filled with either air or water by an infusion pump attached to one end of the segment through the stopper. All tests will be carried out on a horizontal plate and with one end free to move during inflation. Continuous monitoring of the pressure and volume is maintained until bursting. Results are then calculated for all dietary groups and compared.

EXAMPLE 1

Nucleotides from RNA

Enhance Wound Healing In Vivo

The present example demonstrates the utility of the present invention with dietary nucleotides in promoting more rapid on wound healing in vivo. Yeast RNA is employed as an example of the particular nucleotides that may be employed in the practice of the present invention. Nucleotide supplementation is demonstrated to be beneficial for wound healing. The present example also demonstrates the utility of the invention for the promotion of wound healing, and for the promotion of more rapid wound healing, in humans. Dietary formulations and preparations for enhancing the wound-healing process and the rate of wound healing are also provided in the present example.

Wound healing was assessed by hydroxyproline (OHP) measurements in the PTFE matrix of a wound cylinder in a mouse model. OHP level within an implanted wound cylinder of PTFE as indicative of wound healing is an established model for the examination of the wound healing process. Briefly, fifteen Balb/C mice were divided in three groups (5 per group). Each group received one of the following diets and water ad libitum: F-Formula rodent chow, NF-nucleotide-free basal diet (Purina) and NFR-NF diet supplemented with 0.25% yeast RNA (U.S. Biochemicals). Basal diet is composed of casein (21%) as source of protein. This source of protein is unlike chow diet in that the standard chow diet has 23.5% protein from corn, soybean, fish meal, meat, bone meal and milk. Basal diet is made isonitrogenous and isocaloric with chow. Fifteen percent sugar is added to make it isocaloric by adding carbohydrate. Basal diet does not contain any purines or pyrimidines.

All animals received these diets 30 days prior to wound cylinder installation. PTFE wound cylinders were placed subcutaneously in the dorsal midline of each animal under general anesthesia. All animals were continued on their respective diets during the post-operative phase of the study. On the $10^{th}$ post-operative day, all animals were euthanized and the wound cylinders were removed for analysis and frozen until assayed. Wound cylinders were analyzed for hydroxyproline (OHP) content using the previously described method of Woessner. The data from this study is shown in Table 2.

TABLE 2

Wound Hydroxyproline Content in Various Dietary Groups

| Diet Group | mg OHP/cm PTFE mean + sem |
|---|---|
| F | 8.95 + 0.67 |
| NF | 9.19 + 0.69 |
| NFR | 14.84 + 1.00* |

* = significantly different from controls $p<0.001$ vs NF,F

Five animals per group, 2 readings per animal.

OHP-Hydroxyproline

The data of Table 2 demonstrate a significantly lower concentration of wound hydroxyproline in control animals as compared to animals maintained on an RNA-supplemented regimen. Hydroxyproline content in the wound tissue is an experimental indicator of the process of wound repair (Woessner and Hunt et al. 1991) Hydroxyproline is an indicator of collagen measurement. The collagenase activity measurement relates to collagen content at the wound site. Mauch et al. (1989) have shown that increased collagenase gene expression in the wound tissue is inversely proportional to the collagen content. Therefore, increased collagenase activity indicates ongoing degradation of collagen in the matrix and consequently the presence of poor wound healing at an injured site.

As the data in Table 2 demonstrate, the diet containing RNA resulted in a statistically significant increase in OHP at the wound site, as compared to OHP content in nucleotide free diet and standard diet maintained animals. Increased OHP content provides a measure of collagen as the wound site, the data demonstrate that a nucleotide-enriched diet enhances collagen content at the wound site, thus indicating an enhanced amount of collagen available at the site for wound repair. A wound is expected to heal more quickly where more collagen is available.

EXAMPLE 2

Adenine, Uracil and RNA enhance Wound Healing In Vivo

The present example is provided to demonstrate the utility of the invention using adenine as a dietary source of nucleotide in the wound healing promoting formulation of the invention.

Twenty-five Balb/C mice were divided into five test groups (n=5) and housed in groups in the animal care facilities. Each group received one of the following diets ad libertum: F—normal mouse chow, NF—nucleotide free diet, NFR—yeast RNA supplemented diet, NFA—adenine supplemented diet, and NFU—uracil supplemented diet. All groups received these diets for at least 30 days prior to wound cylinder implantation. All animals received water ad libitum.

Polytetrafluorethylene (PTFE, Impra Vascular Graft, 3 mm lumen, 190 mm pore size) wound cylinders (1.5 cm long) were placed subcutaneously in the dorsal midline of each animal under general anesthesia (Methoxyflurane, inhalation). All animals were continued on their test diets. On the tenth post-operative day, all animals were euthanized by cervical dislocation and the would cylinders were removed for analysis.

Wound cylinders were analyzed for hydroxyproline (OHP) content using the method of Woessner. Briefly, approximately 1 cm segments of the wound cylinders were hydrolyzed in 0.5 ml 6 N HCl for 3 hours at 130 C. Samples were cooled and 0.5 ml aliquots were neutralized with the appropriate volume of 1 N NaOH. Each sample was diluted to 5.25 ml with $H_2O$ in order to reduce the total NaCl concentration to below 0.4 M. Each sample was then reacted as described by Woessner.

FIG. 1 reports the results of this study. Adenine, RNA, and uracil all increased the amount of OHP/cm PTFE over both the nucleotide free and the non-supplemented diets. The increases seen for both adenine and RNA were proven to be significant over the nucleotide free diet, while the increase for the adenine supplemented diet was seen to be statistically significant over the non-supplemented diet as well. In fact, the adenine supplemented diet increased the amount of OHP in the wound by close to two times.

PROPHETIC EXAMPLE 3

Preparation of Nucleotide-Containing Therapeutic Composition for Humans

The present example is provided to detail the preparation of a nucleotide-enriched composition suitable for administration to humans. These compositions can contain any combination of nucleotides. However, the inventors have made preliminary observations suggesting that combinations comprising purines and pyrimidines or simply pyrimidines alone may work better than those containing purines alone. This composition can be used as either a diet supplement or, with suitable additions of nutrients, as an enteral or parenteral diet.

For example, a nucleotide-enriched liquid could contain about 0.25% RNA, dissolved in water or another suitable liquid. To make such a preparation, one mixes 2.5 g of RNA (from yeast or another source) with a liter of diluent. It, of course, may be necessary to add additional ingredients to place the liquid in a suitable form for feeding to a patient such as a semi-solid custard or soup.

The nucleotide should be administered at a level of from 0.00034–0.17 g/kg body weight/day. Any concentration of nucleotides that will effectively administer that amount of nucleotides in the particular composition being formulated will be useful. For example, a tablet will likely need a much higher percentage concentration of nucleotides than a custard or other food to administer the required dose.

PROPHETIC EXAMPLE 4

Proposed Methods for Promoting/Enhancing the Rate of Wound Healing in Humans The present prophetic example is provided to outline a proposed methods whereby the nucleotide regimens of the invention may be used in the treatment of humans for the promotion/enhancement of wound healing.

Examples of use of RNA or nucleotide sources as a dietary or topical substrate for enhancing wound healing would include some of the following clinical uses. Note that in the following example, RNA can be substituted for similar levels of purines and/or pyrimidines.

A. RNA in a dose ranging from 0.00034 gm/kg/day to 0.17 gm/kg/day could be provided as part of a complete liquid diet with appropriate calories and protein in the same diet. This diet could be consumed as the sole dietary source or a supplement to a patient who was eating. In a patient whose intestinal function was adequate but who was not capable of eating, the diet could be administered by means of a tube into the stomach or intestinal tract. The major difference between this treatment and other enteral diets is that the RNA would be specifically enhance wound healing in a patient after an injury or after a surgical procedure.

B. RNA in a dose ranging from 0.00034 gm/kg/day to 0.17 gm/kg/day could be provided as an enteral supplement. The supplement could be mixed in water and drunk, or could be administered by an enteral feeding tube. If the patient were taking some food orally, the RNA supplemented could be mixed in custards, gelatin, or soups. Since RNA is virtually tasteless, no artificial flavorings would be required. The advantage of this formulation is that the patient could have very little intestinal function, and yet could assimilate a low volume of fluid containing the required dose of RNA. Thus, even after major gastrointestinal surgery, when most of the calories and protein might be administered intravenously, an oral or enteral RNA supplement to enhance wound healing could be provided.

C. Nucleobases most likely would be administered as nucleosides for parenteral use. This is due to the ionic nature of nucleotides which might impede transport of these substrates across cell membranes. The dose of pyrimidine nucleosides would range from 0.00022 gm/kg/day to 0.12 gm/kg/day delivered parenterally (these concentrations differ from the concentrations of nucleotides only because the nucleosides do not have a phosphate group to add to their weight). The dose of purine nucleosides would range from 0.00022 gm/kg/day to 0.12 gm/kg/day with the precaution that inosine should be substituted from adenosine at higher doses, due to pharmacological effects of adenosine. Specifically, adenosine has been recognized as a participant in the regulation of coronary, cerebral, skeletal and renal blood flows. Therefore, it may be desirable to avoid large doses of adenosine. For a discussion of adenosine's pharmacological effects, please see Belardinelli et al. (1989). These substrates could be administered with total parenteral nutrition or as additives to 5% dextrose or 0.9 M saline solutions administered by peripheral intravenous lines. Depending on the local inflammatory response, these substrates, could also be injected subcutaneously.

D. RNA or nucleosides can be administered topically via salve, an ointment, an impregnated dressing, a sustained release patch, or as a powder. In this application the substrate can be applied directly to the wound to induce enhanced healing. The dose will range from 0.5 mM to 100 mM.

EXAMPLE 5

Topical Applications for Wound Healing in Mice

Balb/c mice were divided into three dietary groups (F=normal mouse chow; NF=nucleotide free mouse chow; and NFR=nucleotide free mouse chow supplemented with yeast RNA). Each group was fed before initiation of wounds. After 4 weeks of feeding, a 4mm punch wound was created on the dorsal surface of each mouse, using a 4mm biopsy punch. The wounds were coated with four different topical agents: 1) saline; 2) uracil {100 $\mu$M concentration); 3) saline+CCM; and 4) Uracil+CCM (CCM=crosslinked collagen mesh). CCM is 'Collagen Permeable Membrane' from Accurate Chemical & Scientific Corporation, catalog no. YIC 152299. Four mm size circles were soaked with appropriate nucleotide or saline solution (4mm punch wounds) and used to dress the wounds.

Twelve groups were formed from these combinations (n=3). Mice were continued on their respective diets. Wounds were observed visually and photographed at four different times during the experimental period of two weeks.

A record was made of the progressive contraction of the wounds and area among the various dietary and treatment groups. Two blinded observations and results are summarized in Table 4.

TABLE 4

| Diet | Topical agent | Relative efficacy |
| --- | --- | --- |
| F | saline | minimal |
| F | uracil | moderate |
| F | saline + CCM | moderate |
| F | uracil + CCM | significant |
| NF | saline | minimal |
| NF | uracil | minimal |
| NF | saline + CCM | moderate |
| NF | uracil + CCM | moderate |
| NFR | saline | moderate |

TABLE 4-continued

| Diet | Topical agent | Relative efficacy |
| --- | --- | --- |
| NFR | uracil | moderate |
| NFR | saline + CCM | significant* |
| NFR | uracil + CCM | significant* |

*With the methods at hand it was difficult to distinguish the observations between the last two groups of NFR fed mice.

These experiments were repeated using a 100 $\mu$M concentration of inosine in place of uracil as the topical agent. The results yielded no significant differences from that which was seen with the uracil.

EXAMPLE 6

Diabetic Mice

Rats were made diabetic by intraperitoneal inoculation of Streptozotocin (55mg/kg body weight). On day 1, if the glucose levels were below 250 mg/dl, then they were reinjected. Only two animals required the second dose. The readings were low on day 0, because the animals were fasted overnight before the induction of diabetes. Subsequent readings were on animals after a 6 hour fast. Table 5 shows resultant blood glucose levels.

TABLE 5

Glucose Levels in Diabetic & Non-Diabetic Dietary Rats

| | Glucose level in mg/dl, mean ± sem | | |
| --- | --- | --- | --- |
| Diet | Day 0 | Day 1 | Day 14 |
| Diabetic | 75.7 ± 3.61 | 306.7 ± 24.21 | 363.0 ± 22.31 |
| Nondiabetic | 62.9 ± 3.33 | 131.4 ± 12.68 | 139.0 ± 1.75 |
| p value | 0.0142* | 0.0001* | 0.0001* |

* = significant at 95%

EXAMPLE 7

Body Weights for Diabetic and Non-Diabetic Rats

The diabetic and nondiabetic rats were divided into two groups of diets: NF (n=14) and NFR (n=15). Each dietary group was divided into two groups: Diabetic (NF:n=7, NFR:n=8); Non-diabetic (NF:n=7, NFR:n=7). The results and body weight for rats on each diet are shown in Table 6.

TABLE 6

Body Weights in Diabetic and Non-Diabetic Punch Wound Rats in Dietary Groups

| | Body weights in grams, mean ± sem | | | |
| --- | --- | --- | --- | --- |
| Diet | Day 0 | Day 5 | Day 8 | Day 15 |
| Diabetic: | | | | |
| NF | 230.5 ± 1.51 | 205.1 ± 15.0 | 227.4 ± 5.61 | 231.4 ± 12.4 |
| NFR | 228.6 ± 1.73 | 241.25 ± 3.5 | 224.1 ± 12.4 | 255.8 ± 9.2 |
| p value | 0.43 | 0.03* | 0.82 | 0.03* |
| Non-diabetic: | | | | |
| NF | 230.1 ± 2.45 | 272.0 ± 3.27 | 285.7 ± 3.76 | 304.4 ± 3.73 |
| NFR | 224.0 ± 1.86 | 259.9 ± 5.74 | 280.6 ± 4.09 | 302.6 ± 3.58 |
| p value | 0.07 | 0.10 | 0.38 | 0.73 |

* = significant at 95%

The RNA enriched diet (NFR) appeared to enhance body weight in the diabetic wounded rats on days 5 and 15.

EXAMPLE 8

Interpretation of Histology Examination in Experimental Diabetic Rats

As may be seen from the histology report that inflammatory evidence was categorized in three types.

Gr. 1—minimal changes with some in epidermis and muscularis serosa.

Gr. 2—moderate changes just under the epidermis

Gr. 3—moderate changes throughout the skin layers.

If one assigns the rat numbers to these categories then take the percentages then the NFR diabetic group fares slightly better than the diabetic NF group. If one looks cumulatively then the difference narrows. However with the given conditions of the experiment, histologic observation shown only a slight difference between the two groups. This is only one experiment and appropriate conditions and modifications of the protocol need to be done. Table 7 shows the skin pathology report.

TABLE 7

Diagnostic Laboratory Health Evaluation
Histopathologic evaluation requested for 58 rat skin sections (29 H&E and 29 Movat stained sections), labeled Rat ADK 1–32 (slides 3, 14, and 19 were not present). Sections were evaluated for relative amounts of inflammation and fibrosis. All sections contained the epidermal, dermal and subcuticular layers.

| Skin # | Diabetic/Non-Diabetic | NF/NFR | Histopathologic Evaluation: |
|---|---|---|---|
| 10 | Diabetic | NFR | No significant histopathologic abnormalities were found. |
| 12 | Diabetic | NFR | |
| 13 | Diabetic | NFR | |
| 24 | Non-Diabetic | NF | |
| 31 | Non-Diabetic | NFR | |
| 32 | Non-Diabetic | NFR | |
| 20 | Non-Diabetic | NF | No significant histopathologic abnormalities were found in the epidermal and dermal layers. Focal area of subcuticular muscle thinning with minimal inflammation was present. |
| 15 | Diabetic | NFR | Small foci of epidermal thickening, with minimal inflammation present in the deep dermis. The underlying subcuticular muscle is thin, and contains a mild mixed inflammatory cell infiltrate |
| 7 | Diabetic | NF | Focal area of superficial dermal fibrosis, underlying a slightly thickened epidermis. The area of fibrosis is composed of almost mature collagen, with minimal inflammation present. The deep dermis in this area contains scattered adnexa (hair follicles) and mild mixed inflammatory cell infiltrates. Underlying subcuticular muscle is interrupted, fragmented, and contains immature connective tissue and minimal to moderate inflammation. |
| 8 | Diabetic | NF | Focal area of superficial dermal fibrosis, underlying a slightly thickened epidermis, and composed of maturing collagen, lacking adnexa, with minimal inflammation present. Subcuticular muscle is interrupted and fragmented in slide 29, and thinned in slide 8, and contains immature connective tissue and minimal to moderate inflammation. |
| 29 | Non-Diabetic | NFR | |
| 2 | Diabetic | NF | Focal area of dermal fibrosis, underlying a slightly thickened epidermis, and composed of maturing collagen, lacking adnexa, with mild to moderate inflammation present. Focal area of subcuticular muscle thinning with minimal to moderate inflammation was present. |
| 22 | Non-Diabetic | NF | |
| 23 | Non-Diabetic | NF | |
| 25 | Non-Diabetic | NFR | |
| 1 | Diabetic | NF | Focal area of dermal fibrosis, underlying a slightly thickened epidermis, and composed of maturing collagen, lacking adnexa, with minimal to moderate inflammation present. Subcuticular muscle is interrupted, fragmented, and contains immature connective tissue and minimal to moderate inflammation. |
| 4 | Diabetic | NF | |
| 5 | Diabetic | NF | |
| 9 | Diabetic | NFR | |
| 11 | Diabetic | NFR | |
| 16 | Diabetic | NFR | |
| 17 | Non-Diabetic | NF | |
| 18 | Non-Diabetic | NF | |
| 26 | Non-Diabetic | NFR | |
| 28 | Non-Diabetic | NFR | |
| 30 | Non-Diabetic | NFR | |
| 6 | Diabetic | NF | focal area of dermal fibrosis, underlying |

TABLE 7-continued

Diagnostic Laboratory Health Evaluation
Histopathologic evaluation requested for 58 rat skin sections (29 H&E and 29
Movat stained sections), labeled Rat ADK 1–32 (slides 3, 14, and 19 were not present).
Sections were evaluated for relative amounts of inflammation and fibrosis. All sections
contained the epidermal, dermal and subcuticular layers.

| Skin # | Diabetic/Non-Diabetic | NF/NFR | Histopathologic Evaluation: |
|---|---|---|---|
| 21 | Non-Diabetic | NF | a slightly thickened, hyperkeratotic |
| 27 | Non-Diabetic | NFR | epidermis with an overlying small foci of necrotic cellular debris and keratin (scab). The dermis in this area is composed of maturing collagen, lacking adnexa, with minimal to moderate inflammation present. Subcuticular muscle is interrupted, fragmented, and contains immature connective tissue and minimal to moderate inflammation. |

EXAMPLE 9

Effects of Diet on Wound Healing

Figure 2:
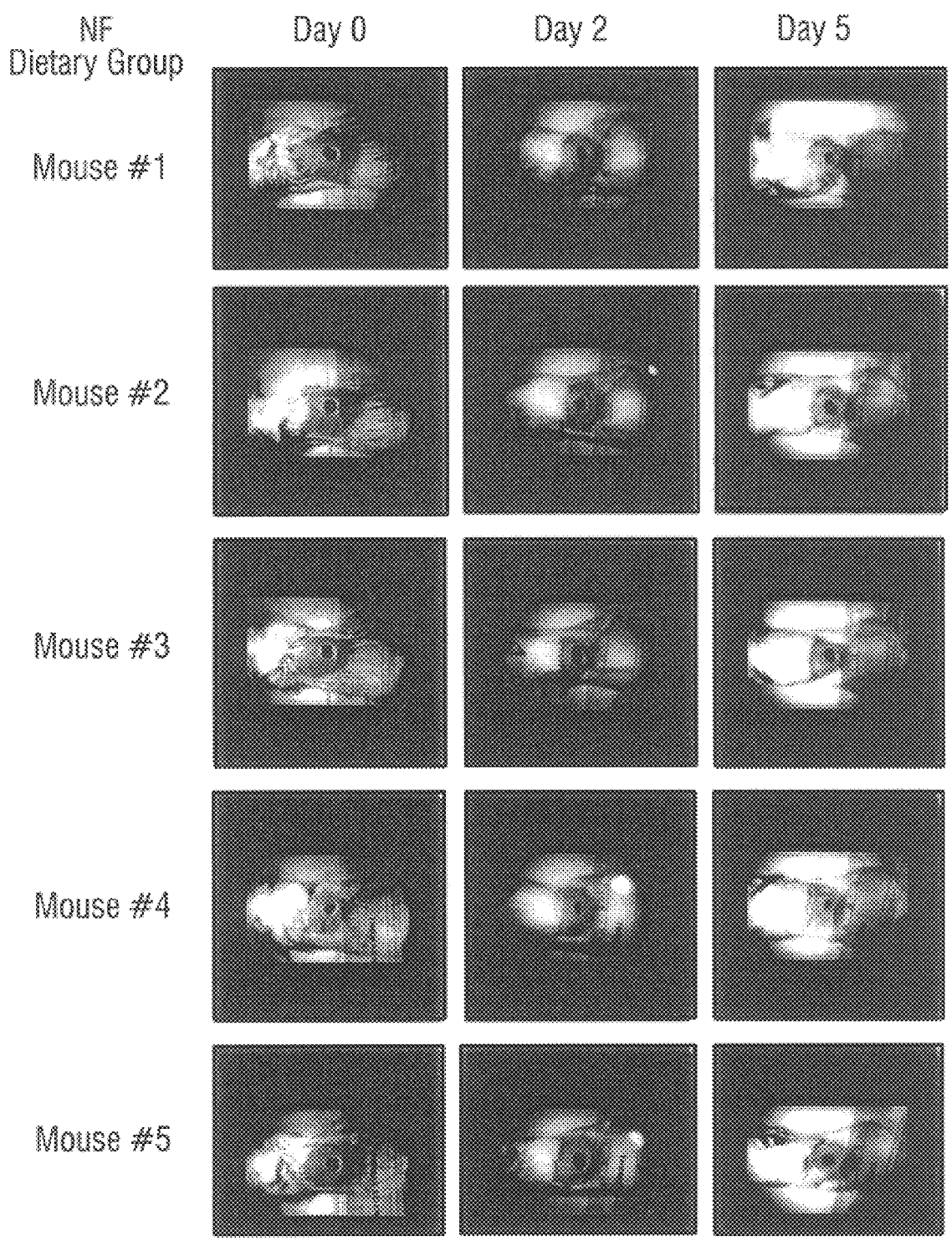
FIGS. 2 and 3 show mice wounds at days 0, 2 and 5.
Figure 3:
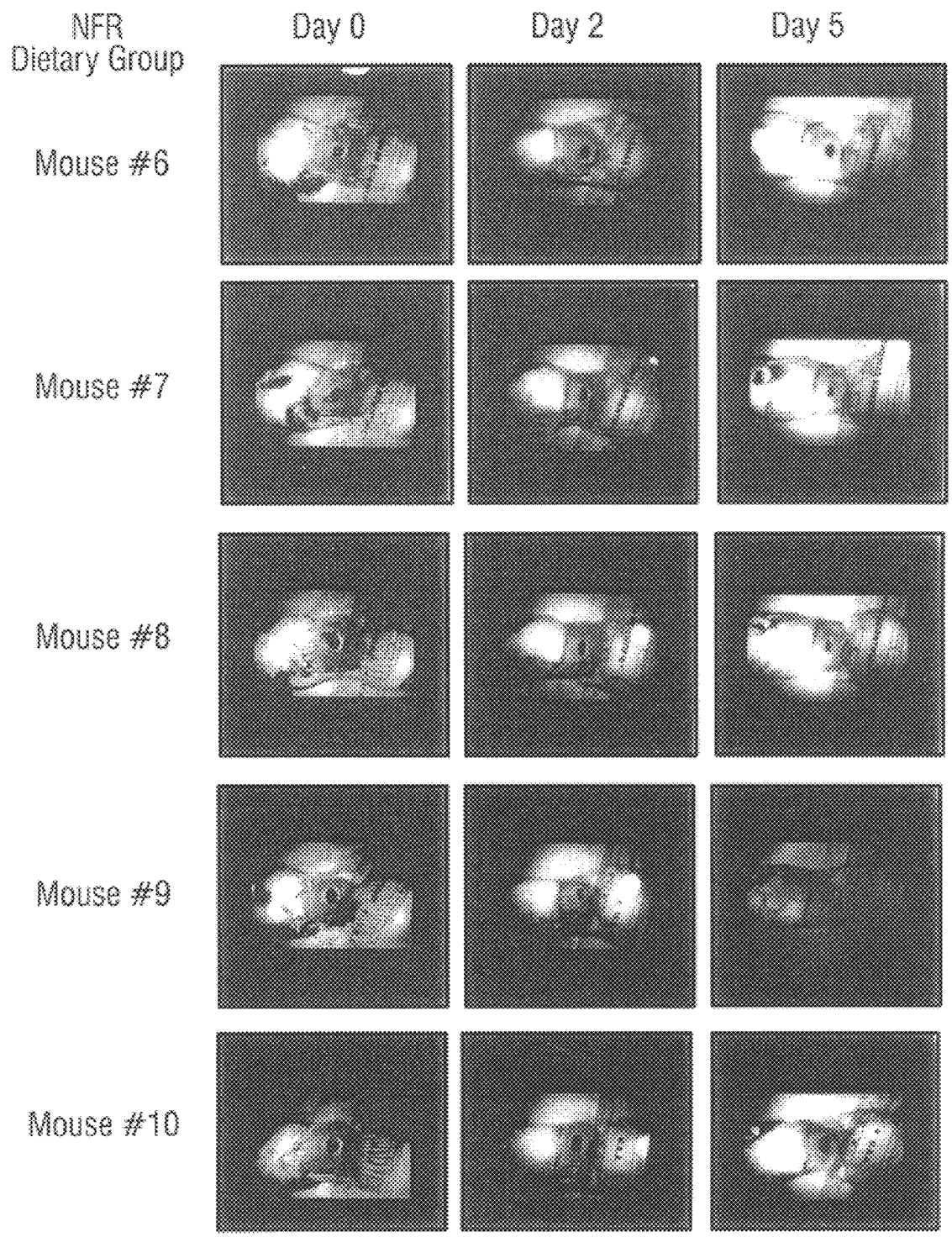
Figure 4:
FIG. 4 shows the wounded mice after two weeks

Wounds were created in anesthetized animals. A 4 mm punch device was used to remove a patch of full thickness skin. Wounds were photographed on day 0, 2 and 5. (See FIGS. 2 and 3). The pictures were transferred to CD-ROM, then digitized using NIH 1.40 Image program to measure the surface area for contraction of the wounds. After two weeks all the wounds appeared closed and the mice were photographed in group (see FIG. 4).

Histology: H. & E. staining as well as Movat staining for collagen/elastin.

NF Group:

1. Mild, multifocal infiltrates of mixed polymorphonuclear and mononuclear cells in and around the area of fibrosis.
2. Mild, diffuse infiltration of mixed inflammatory cells.
3. Moderate, multifocal, infiltration of mixed inflammatory cells with scattered microabscesses.
4. Mild, diffuse infiltration of mixed inflammatory cells.
5. Mild to moderate diffuse infiltration of mixed inflammatory cells.

NFR Group:

6. Moderate, diffuse infiltrations of mixed inflammatory cells with scattered microabscesses.
7. No area of fibrosis in sections examined.
8. No area of fibrosis in sections examined.
9. No area of fibrosis in sections examined.
10. Mild, diffuse infiltration of mixed inflammatory cells.

H. & E. observation indicates that NFR diet is more efficacious than NF diet.

No observable differences in collagen/elastin staining was found in skin sections examined. Table 8 summarizes the surface area of the mouse wounds at day 0, 2 and 5.

TABLE 8

Surface Area of Contracting Wounds in Dietary Mice
on Day 0 and Day 2 and 5 Post Wounding

| | Wound area/1 mm2, mean + sem (%) | | |
|---|---|---|---|
| Diet | Day 0 | Day 2 | Day 5 |
| NF | 21.97 ± 1.92 | 16.36 ± 2.41 | 16.24 ± 2.41 |
| NFR | 21.37 ± 1.53 | 15.18 ± 3.06 | 13.14 ± 4.1 | n = 5/group

It is noted that the nutritional nucleotide addition promotes a more accelerated decrease in wound area.

EXAMPLE 10

Ribonucleotides from RNA Enhance Wound Healing in a Protein Starvation Model This example concerns the use of nucleotides in a protein starvation setting. This would be applicable particularly to patients on dextrose iv during hospital stays in which it would be desirable to maintain immune function.

TABLE 9

Wound Hydroxyproline Content in Protein-Starved or
Nucleotide-Starved or Supplemented Dietary Groups

| Diet Group (n = 18–20) | μg OHP/cm PTFE |
|---|---|
| NF | 32 ± 4 |
| PF | 23 ± 2* |
| PFR | 28 ± 2** |
| NFR | 40 ± 5 |

*$p < 0.05$ vs PFR, NF and NFR
**$p < 0.05$ compared to NFR

The data demonstrate an enhancement in collagen formation even in the absence of dietary protein. Addition of both protein and RNA is desirable to achieve maximal healing effects. This suggests application of such nutritional supplementation to optimize wound healing for patients subject to protein-free and/or a nucleotide-free nutrition. The protein free dietary situation may occur in dextrose iv feeding and in some disease states. A wound will clearly heal faster when RNA is added even in the protein free situation.

Further modifications in alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in these methods and compositions. For example, equivalent elements or materials may be substituted for those illustrated and described herein, and certain features of invention may be utilized independently of the use of other features, all as would be apparent to one skilled in the art after having the benefit of this description of the invention.

REFERENCES

The references listed below are incorporated herein by reference to extent that they supplement, explain, provide a background for or teach methodology techniques and/or compositions employed herein.

Belardinelli et al., The Candiac Effects of Adenosine, Progress in Cardiovascular Diseases, XXXII:73–97 (1989).

Case, S. (1981) U.S. Pat. No. 4,308,257.

Chou et al. (1 984) U.S. Pat. No. 4,486,439.

DeLucchi et al. (1991) "Effects of dietary nucleotides on the fatty acid composition of erythrocyte membrane lipids in term infants," J. Pediatr. Gastroenterol. Nutr., 6(4):568–574.

Faist et al. (1991) "Nutrition and tumor diseases," In: Surgery Nutrition and the Immune System, P. Schauder (Ed.)

Fanslow W. C. et al. (1988) "Effects of nucleotide restriction and supplementation on resistance to experimental murine candidiasis." J. Parent. and Etn. Nutrition. 12:49–52.

Gauri (1983) "Combined preparation with synergistic effect (translation from German," K.K. EP No. 85,084.

Gil Angel H (ES) et al. (1991) "Method for stimulation or repair and regeneration of intestinal gut cells in infants and enhancing the immune response of T-cells," U.S. Pat. No. 4,994,442

Gil Angel H (ES) et al. (1991) "Infant formulas and nutrition products enriched with nucleosides and/or nucleotides and processes for their preparation," U.S. Pat. No. 5,066,500

Goodson W. H. and Hunt T. K. (1982) "Development of a new miniature method for the study of wound healing in human subjects," J. Surg. Res. 33:394–401.

Hunt, Goodson, and Scheuenstuhl, "A strategy for human studies: Thoughts on models" Wound Healing: Ed. H. Janssen, R. Rooman and J.I.S. Robertson, 1991 Wrightson Biomedical Publishing Ltd.

Kulkarni A. D. et al. (1992) "Immunohemopoietic effects of dietary nucleotide restriction in mice," Transplantation 53(2):467–472.

Kulkarni A. D. et al. (1988) "Expression of immune cell surface markers in vivo and immune competence in mice by dietary nucleotides," Transplantation Proc. 21(1):121–124.

Kulkarni A. D. et al., Influence of dietary nucleotide restriction on bacterial sepsis and phagocytic cell function in mice. Archives of Surgery 121:169–172, 1986.

Kulkarni A. D. et al. (1987) "Modulation of delayed hypersensitivity in mice by dietary nucleotide restriction," Transplantation 44(6):847–49.

Mauch, Adelman-Grill, Hatamochi, and Krieg "Collagenase gene expression in fibroblasts is regulated by a three-dimensional contact with collagen" FEBS Letters 250:301–305 (1989).

Nelson T. S. and Anders C. J. (1966) "Dynamic aspects of small intestinal rupture with special consideration of anastomotic strength," Arch. of Surg. 93:309–314.

Peterson J. M. et al. (1987) "Significance of T-lymphocytes in wound healing," Surgery 102(2):300–305.

Pizzini et al. (1990) "Dietary nucleotides reverse malnutrition and starvation-induced immunosuppression," Arch. Surg. 125(1):86–89.

Rudolph F. B. et al. (1990) "Role of RNA as a dietary source of pyrimidines and purines in immune function," Nutrition 6:45–51.

Studt et al. (1984) "Treatment of coccidiosis," U.S. Pat. No. 4,486,439.

Van Buren et al. (1983) "The influence of dietary nucleotides on cell mediated immunity," Transplantation 36:350–352.

Van Buren et al. (1985) "Dietary nucleotides: A requirement for helper/suppressor lymphocytes," Transplantation, 40(6): 694–697.

Van Buren et al. "Role of dietary nucleotide sources in prevention of immune function loss accompanying protein starvation," (In Preparation).

Woessner J. F. Jr. (1961) "The determination of hydroxyproline in tissue and protein samples containing small proportions of this amino acid," Arch. Biochem. Biophys. 93:440–447.

What is claimed is:

1. A method for promoting wound healing in a diabetic subject, said method comprising:

preparing a dietary composition supplemented with one or more compound selected from the group consisting of adenine, uracil, inosine, and adenosine and mixtures thereof in an amount effective for promoting wound healing; and feeding said subject the composition.

2. A method for promoting wound healing in an animal subject to protein deficient nutrition, said method comprising:

preparing a dietary composition supplemented with one or more compound selected from the group consisting of adenine, uracil, inosine, and adenosine and mixtures thereof in an amount effective for promoting wound healing; and feeding said wounded animal with the composition.

3. A method for the promotion of wound healing in a subject, said method comprising:

preparing a composition supplemented with one or more compound selected from the group consisting of adenine, uracil, inosine, and adenosine and mixtures thereof in an amount effective for promoting wound healing; and treating said subject with the composition such that the wound area has increased concentrations of the compound, wherein said treating is by enteral administration.

4. A method for promotion Of wound healing in an animal, said method comprising:

obtaining a crosslinked collagen mesh;

preparing a composition supplemented with one or more compound selected from the group consisting of RNA, uracil and inosine in an amount effective for promoting wound healing;

placing the crosslinked collagen mesh on the wound; and treating said wounded animal with the composition such that the wound area has increased concentrations of the compound.

5. The method of any one of claim 1, 2, 3 or 4 wherein the amount of the composition is sufficient to provide a dose of about 0.0034 to about 0.17 g nucleotide per kg of body weight per day.

6. A method for the promotion of wound healing in a subject, said method comprising:
preparing a composition supplemented with one or more compound selected from the group consisting of RNA, uracil and inosine in an amount effective for promoting wound healing; and
treating said subject with the composition such that the wound area has increased concentrations of the compound, wherein the treating is topical.

7. A method for the promotion of wound healing in a subject, said method comprising:
preparing a composition supplemented with one or more compound selected from the group consisting of RNA, adenine, uracil, inosine, and adenosine in an amount effective for promoting wound healing; and
treating said subject with the composition such that the wound area has increased concentrations of the compound, wherein said treating is by intravascular administration.

8. A method of promoting wound healing in an animal, said method comprising:
preparing a composition comprising a concentration of free pyrimidine bases, nucleosides or nucleotides effective for the promotion of wound healing in a pharmaceutically acceptable carrier; and
treating an animal in need thereof with a therapeutically effective concentration of the composition.

9. The method of claim 8, wherein the animal is a human.

10. The method of claim 8, wherein the wound is a surgical wound.

11. The method of claim 10, wherein the wound is a surgical wound and the composition is administered to the animal as a surgery pretreatment.

12. The method of claim 8, wherein the composition comprises free pyrimidine nucleotides.

13. The method of claim 12, wherein the animal is treated with from about 0.00034 to about 0.17 g nucleotides/kg body weight/day.

14. The method of claim 8, wherein the composition comprises free pyrimidine nucleosides.

15. The method of claim 14, wherein the animal is treated with from about 0.00022 to about 0.12 g nucleosides/kg body weight/day.

16. The method of claim 8, wherein the pyrimidine base may be selected from the group consisting of uracil, thymine and cytosine.

17. The method of any one of claim 1, 2, 3 or 4 wherein the amount of the composition is sufficient to provide a dose of about 0.00022 to about 0.12 g per kg of body weight per day.

18. A method for enhancing the rate of wound healing in an animal comprising administering to an animal in need thereof a therapeutically effective concentration of pyrimidine bases, nucleosides or nucleotides or mixtures thereof formulated in a pharmacologically acceptable carrier.

19. The method of claim 18, wherein the animal is a human.

20. The method of claim 18, wherein pyrimidine nucleotides arc administered to the animal.

21. The method of claim 20, wherein from about 0.00034 to about 0.17 g nucleotides/kg body weight/day is administered.

22. The method of claim 18, wherein pyrimidine nucleosides are administered to the animal.

23. The method of claim 22, wherein the animal is treated with from about 0.00022 to about 0.12 g nucleosides/kg body weight/day.

24. A pretreatment method for enhancing the rate of wound healing in an animal undergoing surgery comprising;
administering a therapeutically effective concentration of pyrimidine bases, nucleosides or nucleotides or mixtures thereof in a pharmacologically acceptable carrier to an animal prior to surgery.

25. The method of claim 24, wherein the pyrimidine bases, nucleosides or nucleotides or mixtures thereof are administered to the animal at least 4 weeks prior to surgery.

26. The method of claim 24, wherein pyrimidine nucleotides are administered.

27. The method of claim 26, wherein the nucleotides are administered in a concentration of about 0.00034 to about 0.17 g/kg body weight/day.

28. The method of claim 24, wherein pyrinidine nucleosides are administered.

29. The method of claim 28, wherein the nucleosides are administered in a concentration of about 0.00022 to about 0.12 g/kg body weight/day.

30. A method of enhancing collagen concentration at a wound site in an animal comprising administering a preparation of pyrimidine bases, nucleosides or nucleotides in a pharmacologically acceptable carrier to the animal.

31. A pretreatment method for enhancing the rate of wound healing in an animal undergoing surgery comprising;
administering a composition comprising pyrimidine bases, nucleosides or nucleotides or mixtures thereof in a pharmacologically acceptable carrier to an animal prior to surgery.

* * * * *

UNITED STATES PATENT AND TRADEMARK OFFICE
CERTIFICATE OF CORRECTION

PATENT NO. : 6,342,484 B1
DATED : January 29, 2002
INVENTOR(S) : Kulkarni et al.

It is certified that error appears in the above-identified patent and that said Letters Patent is hereby corrected as shown below:

Column 24,
Line 57, please delete "Of" and insert -- of -- therefor.

Column 26,
Lines 22 and 45, please delete ";" and insert -- : -- therefor.

Signed and Sealed this

Twenty-fifth Day of June, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

| | | |
|---|---|---|
| PATENT NO. | : 6,342,484 B1 | Page 1 of 1 |
| APPLICATION NO. | : 09/012367 | |
| DATED | : January 29, 2002 | |
| INVENTOR(S) | : Anil D. Kulkarni et al. | |

It is certified that error appears in the above-identified patent and that said Letters Patent is hereby corrected as shown below:

In column 1, lines 8-12, delete
"The United States government has a paid-up license in this invention and the right in limited circumstances to require the patent owner to license others on reasonable terms as provided by the terms of Grant No. RO1-CA35492 awarded by the National Institutes of Health." and insert
--This invention was made with government support under grant number CA035492 awarded by the National Institutes of Health. The government has certain rights in the invention.-- therefor.

Signed and Sealed this

Fifth Day of May, 2009

JOHN DOLL
*Acting Director of the United States Patent and Trademark Office*